US010730080B1

(12) United States Patent
Brown et al.

(10) Patent No.: US 10,730,080 B1
(45) Date of Patent: Aug. 4, 2020

(54) LOW-POWER CLEANING OF UNDERWATER CABLE/ARRAY

(71) Applicant: SPAWAR Systems Center Pacific, San Diego, CA (US)

(72) Inventors: Michael H. Brown, San Diego, CA (US); Nicholas R. Caruso, San Diego, CA (US)

(73) Assignee: United States of America as represented by Secretary of the Navy, Washington, DC (US)

(*) Notice: Subject to any disclaimer, the term of this patent is extended or adjusted under 35 U.S.C. 154(b) by 0 days.

(21) Appl. No.: 16/288,511

(22) Filed: Feb. 28, 2019

(51) Int. Cl.
*B08B 1/00* (2006.01)
*A61L 2/10* (2006.01)
*B08B 7/00* (2006.01)
*B08B 9/023* (2006.01)
*B63G 8/00* (2006.01)
*A61L 2/24* (2006.01)

(52) U.S. Cl.
CPC ............ *B08B 1/002* (2013.01); *A61L 2/10* (2013.01); *A61L 2/24* (2013.01); *B08B 7/0057* (2013.01); *B63G 8/001* (2013.01); *A61L 2202/11* (2013.01); *A61L 2202/14* (2013.01); *A61L 2202/16* (2013.01); *A61L 2202/17* (2013.01); *B63G 2008/004* (2013.01)

(58) Field of Classification Search
CPC ....... B08B 1/002; B08B 7/0057; B08B 9/023; A61L 2/10
See application file for complete search history.

(56) References Cited

U.S. PATENT DOCUMENTS

| | | | |
|---|---|---|---|
| 5,322,569 A | 6/1994 | Titus | |
| 6,311,546 B1 | 11/2001 | Dickinson | |
| 7,713,558 B2 | 5/2010 | Riquelme Salamanca | |
| 9,562,163 B2 | 2/2017 | Lobe | |
| 2006/0189686 A1 | 8/2006 | Martensson | |
| 2006/0216193 A1* | 9/2006 | Johnson | A61N 5/0624 422/24 |
| 2008/0127875 A1* | 6/2008 | Hoogeveen | B08B 9/023 114/312 |
| 2010/0235018 A1* | 9/2010 | Christ | B63C 11/52 701/2 |
| 2014/0083931 A1 | 3/2014 | Chang | |
| 2016/0068240 A1 | 3/2016 | Swain | |
| 2019/0039251 A1* | 2/2019 | Outa | B23K 31/125 |

* cited by examiner

*Primary Examiner* — Kevin Joyner
(74) *Attorney, Agent, or Firm* — Naval Information Warfare Center, Pacific; Kyle Eppele; J. Eric Anderson

(57) ABSTRACT

A low-power system for cleaning an underwater object, comprising an autonomous vehicle configured to move along a surface of an underwater object to be cleaned, the autonomous vehicle including a cleaning device. The cleaning device is configured to remove biofouling from the surface of the underwater object. The autonomous vehicle further includes a variable buoyancy mechanism configured to control a buoyancy of the autonomous vehicle, such that the autonomous vehicle moves up and/or down an underwater object.

12 Claims, 4 Drawing Sheets

LOW-POWER CLEANING OF UNDERWATER CABLE/ARRAY

FEDERALLY-SPONSORED RESEARCH AND DEVELOPMENT

The United States Government has ownership rights in this invention. Licensing inquiries may be directed to Office of Research and Technical Applications, Space and Naval Warfare Systems Center, Pacific, Code 36000, San Diego, Calif., 92152; telephone (619) 553-3001; email: ssc_pac_t2@navy.mil. Reference Navy Case No. 103808.

BACKGROUND OF THE INVENTION

Field of the Invention

The present disclosure relates generally to cleaning and, more particularly, to cleaning of underwater objects, such as underwater cables/arrays.

Description of Related Art

Keeping marine life from growing on underwater objects, such as acoustic arrays or cables, deployed in the water column is a difficult challenge. This biofouling can prevent successful data acquisition and is an irritant for both deployment and recovery.

Older methods of cleaning biofouling involved painting the cables/arrays with an anti-fouling paint, which is expensive and presents health risks. This can be relatively effective for certain scenarios, but the paint may lose its effectiveness after about twelve (12) months of continuous deployment. Further, this paint is a serious health hazard for painting and post paint handling. Finally, this paint is typically cured in ovens, meaning that housings must be masked and painted separately, adding delays to the total project timeline.

SUMMARY OF THE INVENTION

Aspects of the present disclosure provide a low-power system for cleaning an underwater object, comprising an autonomous vehicle configured to move along a surface of an underwater object to be cleaned. The autonomous vehicle includes a cleaning device. The cleaning device is configured to remove biofouling from the surface of the underwater object. The autonomous vehicle further includes a variable buoyancy mechanism configured to control a buoyancy of the autonomous vehicle, such that the autonomous vehicle moves up and/or down a water column.

BRIEF DESCRIPTION OF THE DRAWINGS

The accompanying drawings, which are incorporated in and form a part of the specification, illustrate example embodiments and, together with the description, serve to explain the principles of the invention. In the drawings.

DETAILED DESCRIPTION

Aspects of the present disclosure provide a low-power non-contact system and method for cleaning and preventing biofouling on underwater objects, such as deployed oceanographic underwater cables or arrays. Biofouling is the accumulation of algae, microorganisms and other often undesirable buildup on wet surfaces, including underwater surfaces.

The system and method described herein may employ a cylindrical autonomous vehicle to pass up and down an underwater object, such as a cable or array. The vehicle may include flashing ultraviolet (UV) light emitting diodes (LEDs) that blink or flash at a rate designed to kill the organism growth on the underwater cable/array that prefaces significant fouling. The autonomous vehicle may be ring-shaped, and may use a compressed gas/oil bladder to alter its buoyancy causing it to rise from depth through the water column. When the autonomous vehicle reaches the end of the array, set by depth or a magnet embedded in the cable, it can vent the compressed gas and return slowly to the bottom possibly generating electrical power with an on-board turbine system. This process may continue until the volume of compressed gas is expelled or battery power for the LEDs is no longer available. Based on historical use, it may be possible to determine the optimum number of up-down cleaning cycles required for a particular implementation.

Figure 1:
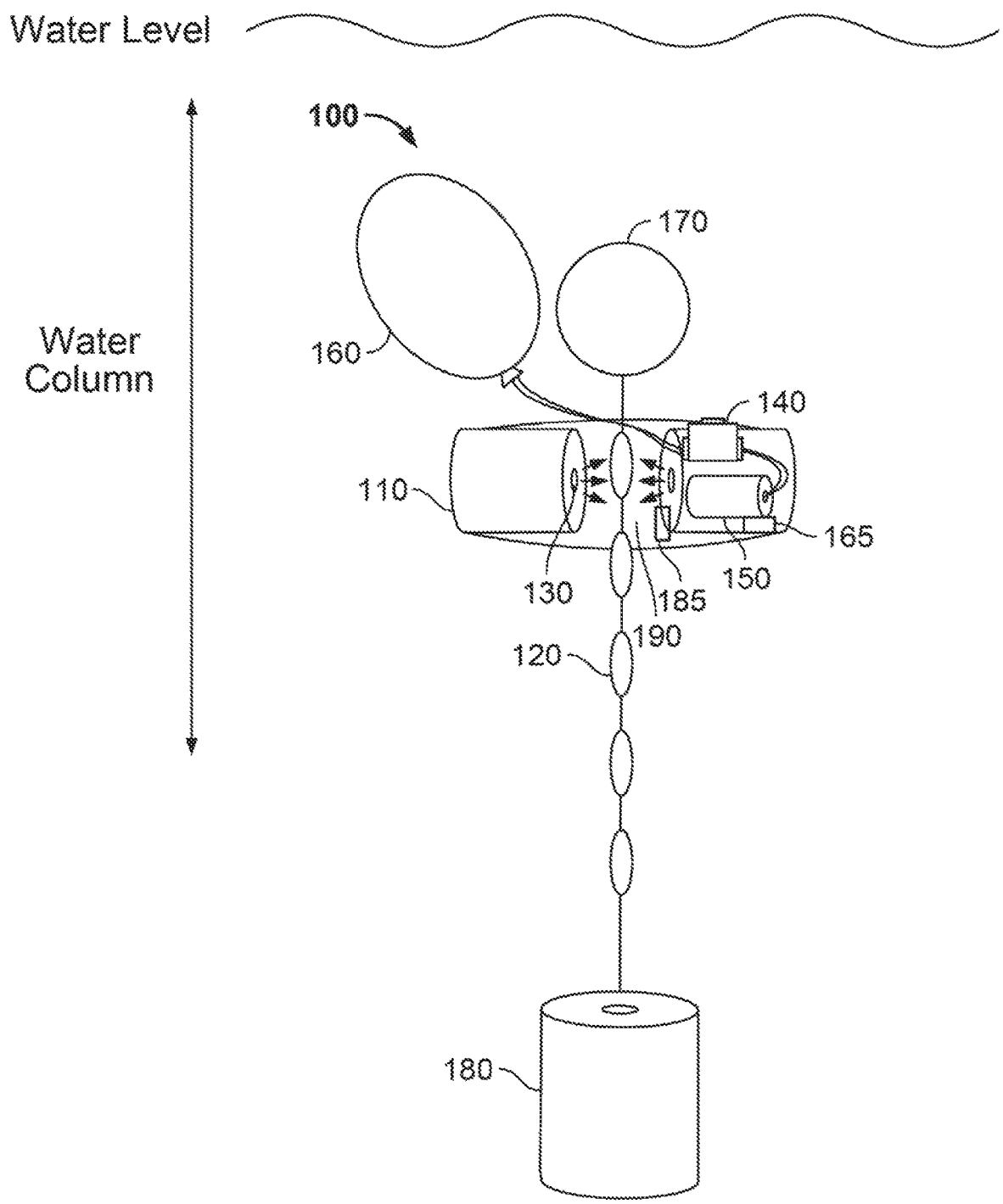
FIG. 1 illustrates a system for low-power cleaning of underwater objects with ultraviolet light emitting diodes (LEDs) in accordance with aspects of the present disclosure.

Referring now to FIG. 1, illustrated is a system for low-power cleaning of undersea cables/arrays with ultraviolet light emitting diodes (LEDs) in accordance with aspects of the present disclosure. The system 100 comprises an autonomous vehicle 110 configured to move along a surface of an underwater object 120 to be cleaned, the autonomous vehicle 110 including a cleaning device 130. The cleaning device 130 is configured to remove organism growth or biofouling from the surface of the underwater object 120. In the present illustration, the underwater object 120 is an underwater cable/array.

In the present illustration, the cleaning device 130 includes one or more flashing ultraviolet (UV) light emitting diodes (LEDs) configured to blink at a rate and time that removes biofouling from the underwater object. The use of LEDs for such purposes is known in the art. Such rates are known in the art. The longer the ultraviolet LEDs of the cleaning device 130 blink, the more likely biofouling is to be removed. It may be desirable to keep the lights blinking as long as possible, but also to conserve power needed for the system 100. Therefore, a duty cycle of fifty percent (50%) on and 50% off may be desirable. In lieu of, or in addition to the UV LEDs, the cleaning device 130 may include brushes configured to remove biofouling from the underwater object, as discussed later in connection with FIGS. 2A and 2B. The brushes may be motor-driven. In lieu of UV LEDs or brushes, the cleaning device 130 may release biocidal chemicals, as known in the art. These biocidal chemicals are configured to remove biofouling from the underwater object. Other means of cleaning may also be used, e.g., ultrasonic means, other mechanical means, other chemical means or any other cleaning method known in the art.

Still referring to FIG. 1, the autonomous vehicle 110 of the system 100 further includes a variable buoyancy mechanism configured to control a buoyancy of the autonomous vehicle, such that the autonomous vehicle moves up and/or down a water column along an underwater object. As shown by the water level, the system 100 is below the water level, and is therefore, underwater. Variable buoyancy is implemented via a solenoid 140 that is operably coupled to an air tank. The solenoid 140 may start and/or stop an air release from an air tank 150 to an air bladder 160. The air tank 150 may contain compressed air, another gas, or a liquid or any other element that can be used to vary buoyancy. Air bladder 160 is configured to receive the air from the air tank 150. The variable buoyancy mechanism may further include a ballast tank and valve mechanism (not shown) such that the air tank 150 can be flooded or purged. In lieu of the autonomous vehicle 110 being moved by a variable buoyancy mechanism, the autonomous vehicle 110 may move substantially up and down along the water column and/or the underwater object under the power of an underwater thrust mechanism 165 such as an onboard turbine engine or other powered means.

The system further includes a fixed buoyancy mechanism 170 configured to cause the underwater object 120 to maintain or have a substantially vertical position in a body of water. In the present illustration, the fixed buoyancy mechanism 170 is a float attached to a first end of the underwater object 120. In order to aid in maintaining the substantially vertical position of the system 100, a sensor bottle 180 is further configured to cause the underwater object 120 to maintain a substantially vertical position in a body of water. The sensor bottle 180 is attached to a second end of the underwater object 120. Sensor bottle 180 may be used to contain relevant acoustics processing electronics and storage media for an underwater object 120 such as the illustrated underwater cable/array. In this implementation, in lieu of sensor bottle 180, another form of anchor or tethering device would be sufficient to ensure the underwater object 120 is oriented substantially vertically in the water column.

The system 100 further includes a magnet 185 configured to indicate a presence of an array node. The magnet 185 may activate the cleaning device 130 for a predetermined period after the magnet indicates the presence of an array node. In this connection, the magnet 185 may signal the beginning of an array node magnetically and then turn the cleaning device 130 on for a set length of time after that, which saves power by only focusing the UV light on the nodes and allowing the cable to foul, not affecting the acoustic properties of the node.

In the present illustration, the autonomous vehicle 110 includes a cylindrical opening 190 therein. Thus, the autonomous vehicle 110 may be ring-shaped and make a full circle around the underwater object 120. The cylindrical opening 190 is configured to permit disposition therethrough of the underwater object 120.

The present system may be used to extend the life of deployed arrays. It is non-toxic, reliable, and reusable. The system 100 may be used for non-contact cleaning of acoustic arrays. The system 100 is also adjustable to different node sizes pertaining to an underwater object 120.

Figure 2A:
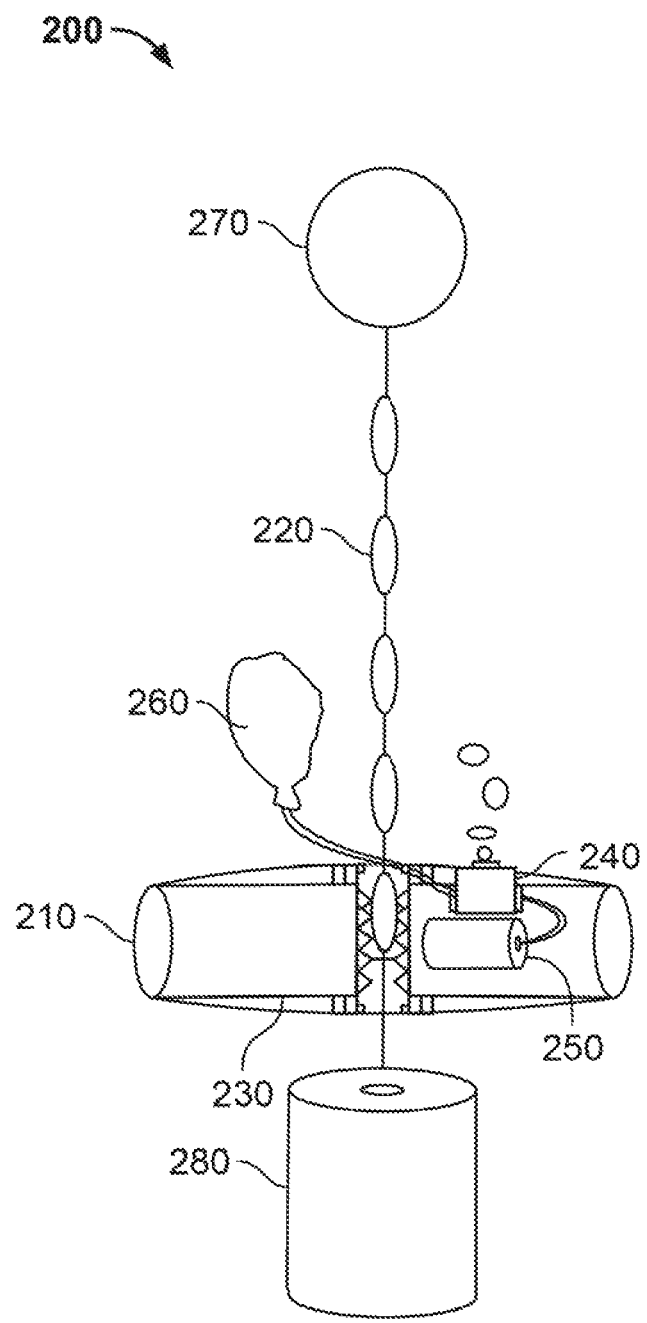
FIG. 2A illustrates a system for low-power cleaning of underwater objects with brushes and an empty air bladder in accordance with aspects of the present disclosure.
Figure 2B:
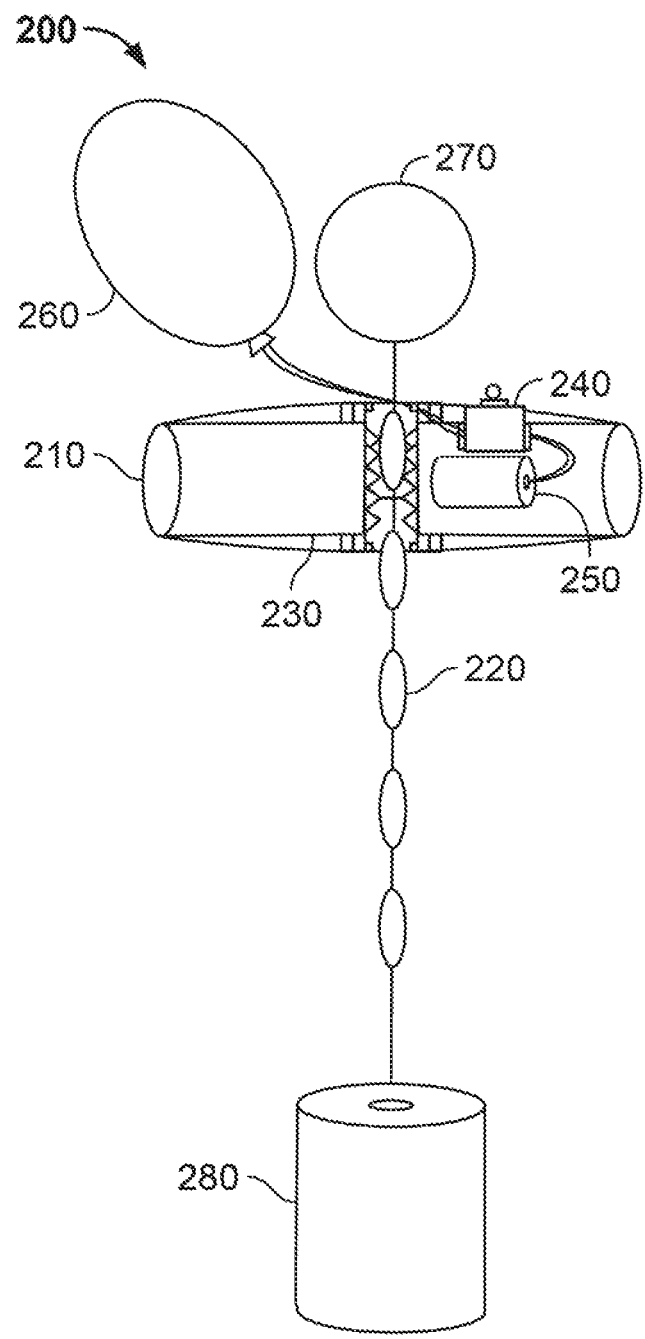
FIG. 2B illustrates the system of 2A with brushes and an inflated air bladder in accordance with aspects of the present disclosure.

Referring now to FIG. 2A, illustrated is a system for low-power cleaning of undersea cables/arrays with brushes and an empty air bladder in accordance with aspects of the present disclosure. FIG. 2B shows the same system of FIG. 2A, but with an inflated air bladder.

Referring to FIGS. 2A and 2B together, the system 200 comprises an autonomous vehicle 210 configured to move along a surface of an underwater cable/array 220 to be cleaned, the autonomous vehicle 210 including a cleaning device 230, the cleaning device 230 being configured to remove organism growth or biofouling from the surface of the underwater cable/array 220.

The cleaning device 230 includes one or more brushes that remove biofouling from the underwater cable/array 220.

Still referring to FIG. 2A, the autonomous vehicle 210 of the system 200 further includes variable buoyancy functionality, which is implemented via a three-way solenoid 240 that is operably coupled to an air tank 250. The three-way solenoid 240 may start and/or stop an air release from an air tank 250 to an air bladder 260. The air tank 250 may contain compressed air, another gas, or a liquid or any other element that can be used to vary buoyancy.

In the illustration of FIG. 2A, the air bladder 260 is empty. However, air bladder 260 is configured to receive the air from the air tank 250. FIG. 2B shows the air bladder 260 in an inflated state.

Referring to FIGS. 2A and 2B together, the system 200 further includes a float 270 configured to cause the underwater cable/array 220 to maintain a substantially vertical position in a body of water. In the present illustration, the float 270 is attached to a first end of the underwater cable/array 220. In order to aid in maintaining the substantially vertical position of the system 200, a sensor bottle 280 is further configured to cause the underwater object 220 to maintain a substantially vertical position in a body of water. The sensor bottle 280 is attached to a second end of the underwater object 220.

In the present illustration, the autonomous vehicle 210 includes a cylindrical opening 190 therein. The cylindrical opening 290 is configured to permit disposition therethrough of the underwater cable/array 220. The autonomous vehicle 210 may be designed to move solely up and down, or it may have horizontal motion capabilities which may be implemented via a motor or other power source.

Figure 3:
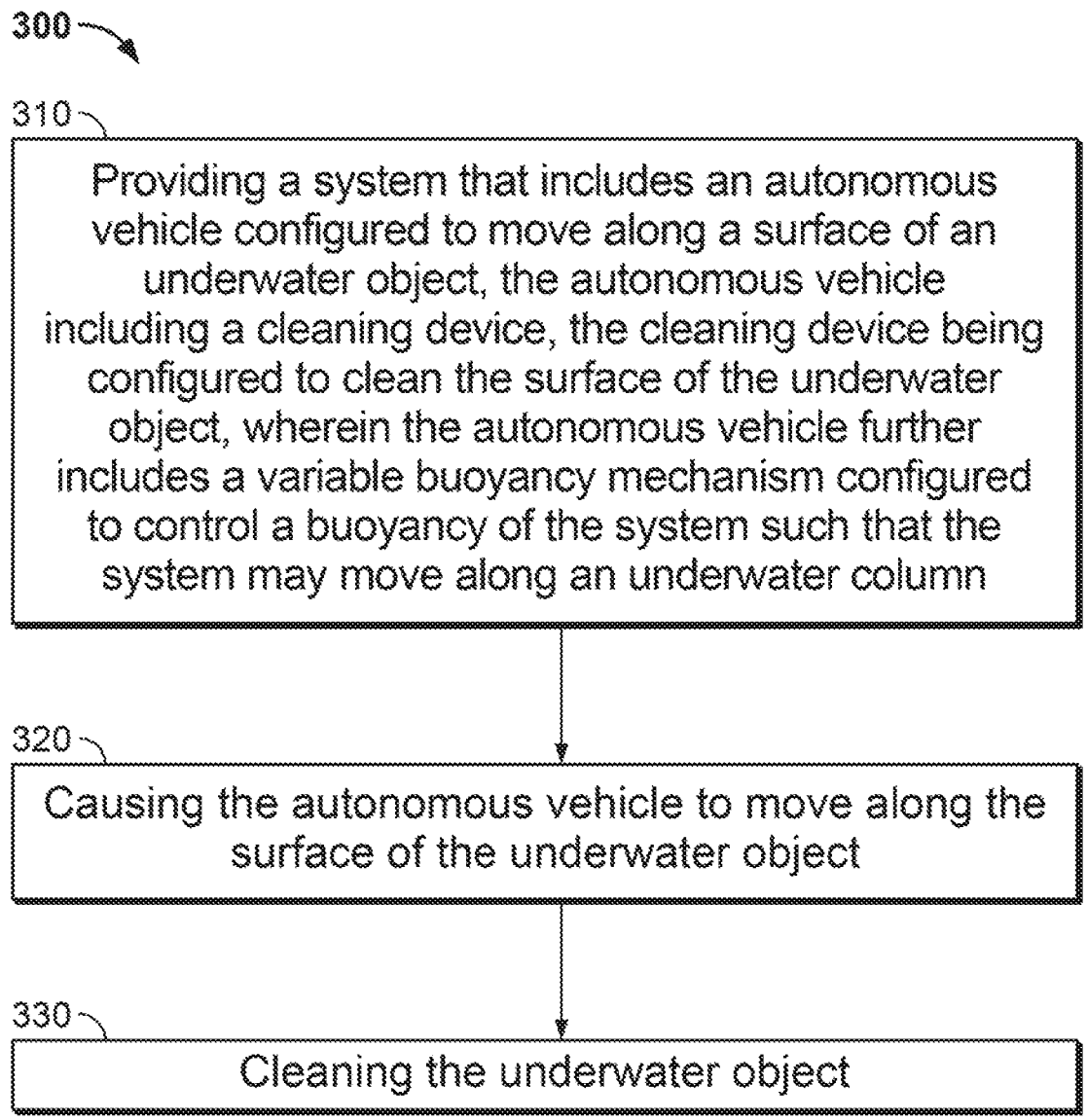
FIG. 3 illustrates a flow chart for a method for low-power cleaning of underwater objects in accordance with aspects of the present disclosure.

Referring now to FIG. 3, illustrated is a flow chart for a method for low-power cleaning of undersea objects in accordance with aspects of the present disclosure. At step 310, the method includes providing a system for cleaning an underwater object that has an autonomous vehicle configured to move along a surface of an underwater cable/array, the autonomous vehicle including a cleaning device, the cleaning device being configured to clean the surface of the underwater object, wherein the autonomous vehicle further includes a variable buoyancy mechanism configured to control a buoyancy of the system such that the system may move up and down a water column. The variable buoyancy mechanism may further include a solenoid, an air tank that contains air, an air bladder configured to receive the air from the air tank, and a solenoid operably coupled to the air tank, the solenoid being configured to start and/or stop an air release from the air tank to the air bladder.

At step 320, the method includes causing the autonomous vehicle to move along the surface of the underwater object, which may be an underwater cable/array. At step 330, the method includes cleaning the underwater cable/array. The step of cleaning the underwater object may include the step of causing one or more ultraviolet light emitting diodes to flash at a rate and time that removes biofouling from the underwater object. For example, the duty cycle of the flashing LEDs may be 50% on and 50% off. Alternatively, the step of cleaning the underwater cable/array may include the step of brushing the underwater object to remove biofouling from the underwater cable/array.

The cleaning device may be activated by indicating, via a magnet, a presence of an array node. In response to the indicating step, the system may activate the cleaning device for a predetermined period after the magnet indicates the presence of an array node.

In order to facilitate cleaning of the underwater object, the method may include causing, via e.g., a fixed buoyancy mechanism and a sensor bottle, the underwater object to maintain a substantially vertical position in a body of water.

Cleaning may be further facilitated by the structure of the autonomous vehicle which may include a cylindrical opening therein. The cylindrical opening is configured to permit disposition therethrough of the underwater object.

The foregoing description of various embodiments have been presented for purposes of illustration and description. It is not intended to be exhaustive or to limit the system and method to the precise forms disclosed, and obviously many modifications and variations are possible in light of the above teaching. The example embodiments, as described above, were chosen and described in order to best explain the principles of the system and method and their practical application to thereby enable others skilled in the art to best utilize them in various embodiments and with various modifications as are suited to the particular use contemplated. It is intended that the scope of the invention be defined by the claims appended hereto.

What is claimed as new and desired to be protected by Letters Patent of the United States is:

1. A low-power system for cleaning an underwater cable/array, comprising:
    an autonomous vehicle configured to move along a surface of the underwater cable/array, the autonomous vehicle including a cleaning device, the cleaning device being configured to remove biofouling from the surface of the underwater cable/array, wherein the autonomous vehicle further includes a variable buoyancy mechanism configured to control the position of the autonomous vehicle, such that the autonomous vehicle moves along the underwater cable/array;
    a magnet configured to indicate a presence of an array node;
    a fixed buoyancy mechanism configured to cause the underwater cable/array to maintain a substantially vertical position in a body of water, wherein the fixed buoyancy mechanism is attached to a first end of the underwater cable/array; and
    wherein the system is configured to activate the cleaning device for a predetermined period after the magnet indicates the presence of the array node.

2. The system of claim 1, wherein the autonomous vehicle includes a cylindrical opening therein, the cylindrical opening being configured to permit disposition therethrough of the underwater cable/array.

3. A low power system for cleaning underwater cables/arrays, comprising:
    an autonomous vehicle configured to move along a surface of an underwater cable/array, wherein the autonomous vehicle includes:
        a cleaning device, the cleaning device being configured to remove biofouling from the surface of the underwater cable/array;
        a variable buoyancy mechanism configured to control a buoyancy of the autonomous vehicle such that the autonomous vehicle may move up and down a water column, wherein the autonomous vehicle includes a cylindrical opening therein, the cylindrical opening being configured to permit disposition therethrough of the underwater cable/array;
    a fixed buoyancy mechanism configured to cause the underwater cable/array to maintain a substantially vertical position in a body of water; and
    a magnet configured to indicate a presence of an array node, wherein the system is configured to activate the cleaning device for a predetermined period after the magnet indicates the presence of an array node.

4. The system of claim 3, wherein the variable buoyancy mechanism further includes a solenoid, an air tank that contains air, an air bladder configured to receive the air from the air tank, and a solenoid operably coupled to the air tank, the solenoid being configured to start and stop an air release from the air tank to the air bladder.

5. The system of claim 3, wherein the cleaning device includes one or more flashing ultraviolet light emitting diodes configured to blink at a rate and for a time configured to clean the underwater cable/array.

6. The system of claim 3, wherein the cleaning device includes brushes.

7. A low-power system for cleaning an underwater cable/array, comprising:
    an autonomous vehicle that includes a cleaning device, which is configured to remove biofouling from the surface of the underwater cable/array, and an underwater propulsion unit selected from the group consisting of a variable buoyancy mechanism and a thrust generation mechanism, wherein the underwater propulsion unit is configured to control the position of the autonomous vehicle, such that the autonomous vehicle is configured to move along the underwater cable/array;
    a magnet configured to indicate a presence of an array node, wherein the system is configured to activate the cleaning device for a predetermined period after the magnet indicates the presence of the array node.

8. The system of claim 7, wherein a separate magnet is embedded in the cable/array near each node.

9. The system of claim 7, wherein the magnet is mounted to the autonomous vehicle.

10. The system of claim 7, wherein the underwater cable/array includes a fixed buoyancy mechanism configured to cause the underwater cable/array to maintain a substantially vertical position in a body of water.

11. The system of claim 7, wherein the autonomous vehicle is configured to move horizontally along the underwater cable/array.

12. The system of claim 7, wherein the cleaning device includes one or more flashing ultraviolet light emitting diodes configured to blink at a rate and for a time configured to clean the underwater cable/array.

* * * * *